United States Patent [19]

Whelchel et al.

[11] 4,149,650

[45] Apr. 17, 1979

[54] STERILIZED STORAGE CONTAINER

[75] Inventors: Robert C. Whelchel, Newport Beach, Calif.; Roger S. Sanderson, 24662 Santa Clara, Dana Point, Calif. 92629

[73] Assignee: Roger S. Sanderson, Dana Point, Calif.

[21] Appl. No.: 827,992

[22] Filed: Aug. 26, 1977

Related U.S. Application Data

[63] Continuation of Ser. No. 640,924, Dec. 15, 1975, abandoned.

[51] Int. Cl.² .............. A61L 3/00; B65D 51/00; B65D 55/00
[52] U.S. Cl. ............... 220/201; 137/DIG. 2; 206/497; 206/509; 220/231; 220/326; 220/378; 251/61.4
[58] Field of Search ............... 215/262, 260, 270, 343, 215/341, 307, 35 S; 137/860, 468, DIG. 2, 508, 526; 206/497, 508, 509; 220/201, 203, 231, 326, 378, 206, 208, 209; 251/61.4; 21/83, 104, 105

[56] References Cited

U.S. PATENT DOCUMENTS

| | | | |
|---|---|---|---|
| 795,626 | 7/1905 | Lampman | 215/260 |
| 933,122 | 9/1909 | Schram | 215/307 |
| 1,244,469 | 10/1917 | Hammer | 215/270 |
| 1,321,205 | 11/1919 | Hammer | 215/270 |
| 1,486,336 | 3/1924 | Heusser | 220/326 |
| 1,688,237 | 10/1928 | Joncha | 137/508 X |
| 1,700,958 | 2/1929 | Staunton | 215/262 |
| 1,862,560 | 6/1932 | Willcutt et al. | 215/262 |
| 1,898,262 | 2/1933 | Packer | 220/326 X |
| 1,931,911 | 10/1933 | White | 53/11 |
| 1,946,872 | 2/1934 | Muhleisen | 220/231 X |
| 1,975,012 | 9/1934 | McKinnis | 426/402 |
| 2,008,835 | 7/1935 | Rawcliffe | 137/468 X |
| 2,092,445 | 9/1937 | Doulgheridis | 220/367 X |
| 2,117,151 | 5/1938 | Cowan | 220/340 |
| 2,117,228 | 5/1938 | Stuchbery | 220/340 |
| 2,187,396 | 1/1940 | Glocker | 215/262 |
| 2,298,814 | 10/1942 | Weis | 220/380 |
| 2,326,209 | 8/1943 | Eggerss | 220/306 x |
| 2,443,506 | 6/1948 | Hohl et al. | 215/346 |
| 2,455,305 | 11/1948 | Heva | 137/468 X |
| 2,457,867 | 1/1949 | Chambers | 53/79 |
| 2,514,458 | 7/1950 | Sinz | 137/508 X |
| 2,526,974 | 10/1950 | Schipanski | 21/98 |
| 2,565,361 | 8/1956 | Elm | 220/201 |
| 2,591,767 | 4/1952 | Andres | 220/203 |
| 2,635,630 | 4/1953 | Cornelius | 137/526 X |
| 2,715,251 | 8/1955 | Vischer, Jr. | 21/98 |
| 2,732,972 | 1/1956 | Anschicks | 220/335 X |
| 2,786,245 | 3/1957 | Steinbock, Jr. | 21/105 |
| 2,990,971 | 7/1961 | Enell | 220/303 X |
| 2,997,397 | 8/1961 | Doulgheridis | 215/355 X |
| 3,064,853 | 11/1962 | Lents et al. | 220/358 |
| 3,145,724 | 8/1964 | Pelzer | 137/526 X |
| 3,247,957 | 4/1966 | Kemble | 206/440 |
| 3,285,409 | 11/1966 | Loran | 206/564 X |
| 3,297,260 | 1/1967 | Barlow | 137/496 X |
| 3,331,105 | 7/1967 | Gordon | 206/497 X |
| 3,411,660 | 11/1968 | La Farge | 220/357 X |
| 3,504,823 | 4/1970 | Logomasini | 220/306 |
| 3,533,670 | 10/1970 | Karnikyen | 21/105 X |
| 3,561,918 | 2/1971 | Ray | 21/84 |
| 3,618,814 | 11/1971 | Nagroski | 220/358 |
| 3,621,951 | 11/1971 | Schmid | 137/468 X |
| 3,672,916 | 6/1972 | Virnig | 229/43 X |
| 3,697,223 | 10/1972 | Kovaleik et al. | 21/105 X |
| 3,954,178 | 5/1976 | Mason, Jr. | 206/509 X |

FOREIGN PATENT DOCUMENTS 828946 12/1951 Fed. Rep. of Germany ............ 215/260
1006083 4/1952 France ...................................... 215/262

Primary Examiner—William Price
Assistant Examiner—Allan N. Shoap
Attorney, Agent, or Firm—Knobbe, Martens, Olson, Hubbard & Bear

[57] ABSTRACT

A storage container for maintaining the sterilized condition of instruments or other articles. The container has a receiving tray and a lid with a unique sealing element that not only provides an excellent seal but also enhances the seating of the lid on the tray portion. Means are placed adjacent the interface of the lid with the tray for holding the lid above the tray during the sterilization process and for releasing the lid to seat in sealing engagement with the tray after the sterilization process. Mounted within the container is a combination relief and release valve to respectively control the amount of vacuum within the container and to release the vacuum in order to allow access to the interior of the container to remove the instruments or articles therein.

13 Claims, 5 Drawing Figures

STERILIZED STORAGE CONTAINER

This is a continuation, of Ser. No. 640,924, filed Dec. 15, 1975, now abandoned.

BACKGROUND OF THE INVENTION

The most commonly used method for sterilizing surgical instruments and other medical items is to place them in towels which are enclosed in a sheet and taped shut for placement in a sterilizing autoclave. Steam within the autoclave penetrates the porous materials surrounding the instruments and sterilizes the instruments. The moisture is removed by a drying cycle in the autoclave. The sterile package of medical instruments is then loaded onto a plastic covered cart and transported through unsterile hallways to less than sterile wards for use in hospital rooms or to be placed on a shelf for future use. If the pack has not been used in twenty days, it must be returned to the autoclave for resterilization. Two-thirds of the sterilization workload in many hospitals is for items that were not used within the shelf life of the pack. The average cost expended in an autoclave load is fairly significant and presents a very inefficient process with considering the high percentage of nonuse, requiring expensive resterilization.

In addition to nonuse, another factor which reflects the shortcoming of the towel arrangement is that, unless adequate labeling is used, the contents within the towel are unknown. Once the package is opened to check the contents, the sterilization is lost unless the contents are immediately used. Therefore, if the contents are not what the user desires, then the sterilization of that particular package must be repeated.

Some of the prior art proposes placing the packs of instruments from the autoclave into plastic bags to keep contamination away and, hence, prolong the sterile shelf life of the package. These bags are vulnerable to puncture and contain contaminated room air when they receive the sterilized packages from the autoclave.

Although several attempts have been made to improve the system for containing sterilized medical items, they have not proved to be satisfactory and the old approach of wrapping items in towels is believed to still be the method most widely used. U.S. Pat. No. 3,697,223-Kovalcik discloses a system which is a step in the right direction, but remains inadequate. That patent discloses a transparent plastic container, so that items are visible while within the container and the items can be sterilized if stored within the same container. However, a fundamental shortcoming of the arrangement disclosed in that patent is the inadequacy of maintaining sterilization. The lid is said to be tight fitting, but it does not actually provide a seal between the lid and cover. It is suggested that autoclaving tape be utilized to seal the lid to the container; however, such tape does not provide a permanent seal. More significantly, that patent shows holes in the lid for circulation during sterilization and no provision is made for closing the holes. Thus a tight fit between the lid and the container or the use of tape would seem to be of no avail.

SUMMARY OF THE INVENTION

The present invention comprises a reusable container which will automatically seal itself in response to certain specified environmental conditions or in response to time controlled means. The container has a tray base and a lid with a sealing element designed to provide a vacuum tight seal between the lid and base. The base has extending from its upper edge an angled lip or flange which receives the generally vertical extending sealing gasket attached to the lid to provide the sealing engagement between the lid and the base. The generally vertical orientation of the sealing gasket in conjunction with the angled flange on the tray portion provide a centering means for the lid to fit properly over the base.

Mounted within the base are a pair of fuses which extend above the top edge of the base to act as posts on which the lid will rest and establish a space between the lid and the base, permitting the entrance of a sterilizing environment into the base containing the instruments to be sterilized. The fuses are designed to collapse after a certain period of time or when subjected to a specified environment such as within an autoclave or another sterilizing environment. This permits the lid to close on the base. Also located between the lid and the base are resilient members which bias the lid into engagement with the base and provide a positive positioning force on the lid against the fuse posts.

Mounted within a recess of the container lid a self-contained diaphragm valve to act as a relief and a release valve. The relief aspect of the valve is to control the amount of vacuum which may exist within the container to avoid any possible damage to the container should the vacuum reach too high levels. Further the release portion of the valve is used manually to gain access within the container which is held tightly in sealed condition by the vacuum.

The use of a clear sturdy reusable container that can withstand the temperatures and pressures within a sterilizing environment, of for instance an autoclave, provides an ideal method of maximum efficiency and minimum cost of sterilizing and storing supplies. The container and lid arrangement is designed to allow the sterilizing steam to contact the entire box including the upper edge of the base. However, the fuse or timing means automatically allows the lid to seal against the base prior to the opening of the autoclave door and return to ambient temperature conditions. By closing the lid under low pressure conditions, a vacuum in the box is provided when room pressure exists around the box. The vacuum remains until the box is opened for use of the instruments therein. The shelf life of such a box is as long as the vacuum is maintained which is considerable. The box eliminates the need for resterilization of unused items every 20 days. It also allows the user of the contents to see what is within the box, eliminating many misopened parcels that now are sent back to the autoclave unnecessarily. The box also provides a desirable sterile environment for the shipment of articles such as heart valves and other medical prostheses. It is envisioned that the container may also be used for the storage of items such as dental instruments and equipment as well as any item in which it is desirable to maintain a clean and sterile environment, such as in the aerospace industry.

DETAILED DESCRIPTION OF THE INVENTION

Figure 1:
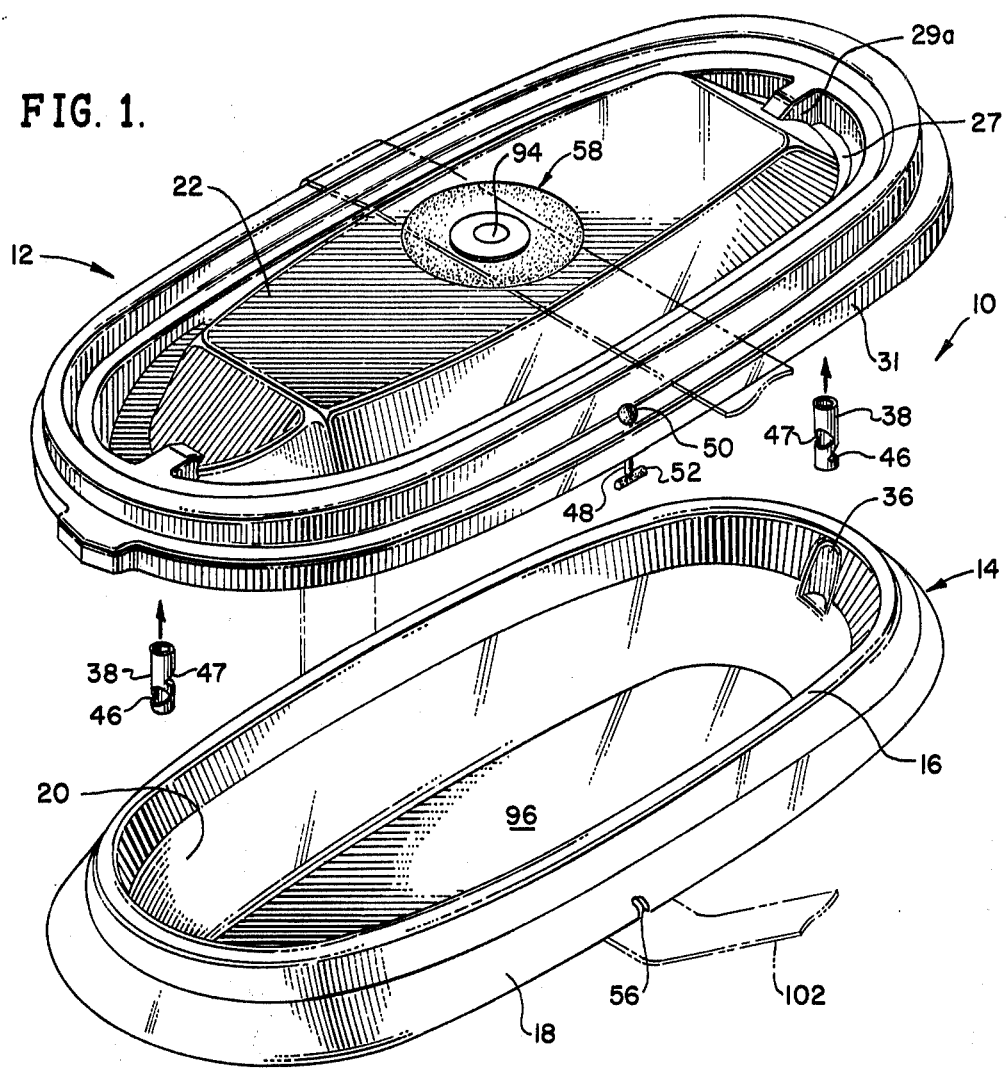
FIG. 1 is a perspective exploded view of the lid and the base tray of the invention.

FIG. 1 shows the container 10 having a lid 12 and a base or tray portion 14. Located around the rounded upper edge 16 on the sidewalls of the base is a downwardly extending angular flange 18 which is shown also in FIG. 2. The base 14 and the lid 12 define a chamber or receptable area 20 for the receipt of instruments or other articles to be sterilized. The preferred general shape of the base and lid is oval or racetrack which provides added strength as well as a more efficient sealing arrangement, in comparison to rectangular.

Figure 2:
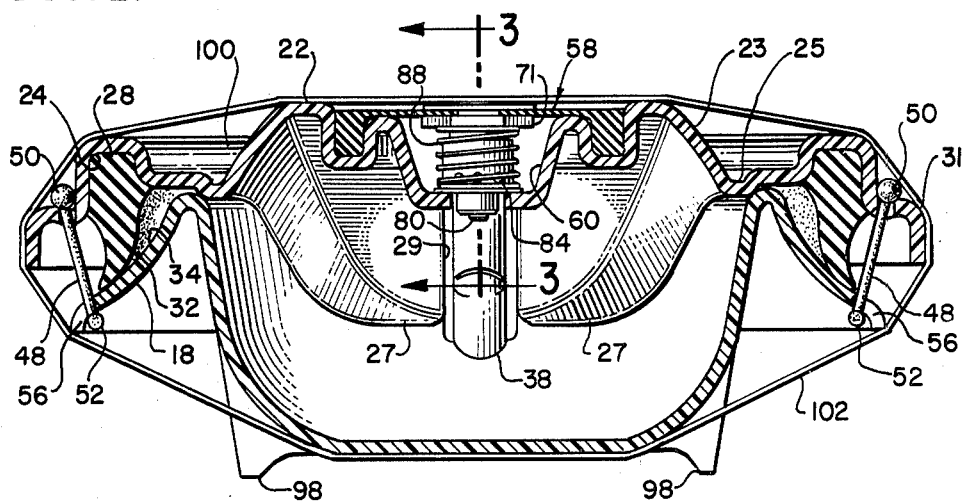
FIG. 2 is a sectional view taken laterally through the container with the lid in closed position.

The lid 12, as shown in FIGS. 1 and 2, has various contours which serve a variety of functions and is also easy to mold and clean. The lid has a flat raised central portion 22 which faciltates stacking of containers. The central portion is supported by downwardly and outwardly sloping curved walls 23 leading to a depending rib 25 which extends around the lid spaced inwardly from the lid periphery 31. The rib 25 is sized to fit within the base 14 and serve as a seat for the lid when it is fully closed.

Figures 4, 5:
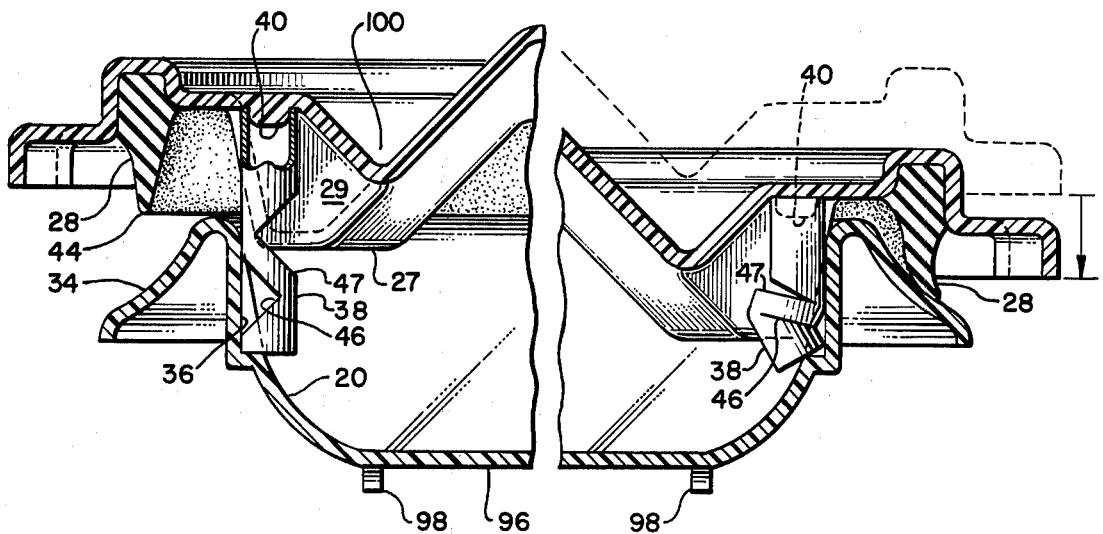
FIG. 4 is a partial, longitudinal sectional view of the lid and base tray portion with the fuse maintaning a space between the lid and the base.
FIG. 5 is a partial longitudinal sectional view of the lid and base showing the fuse removed and the lid in engagement with the base.

On each end of the lid is a pair of guide sections 27 which are circumferentially aligned with the rib 25 but which depend further into the base than rib 25, as may be seen in FIGS. 4 and 5. Extending between each pair of guide sections is a downwardly opening slot 29 defined by lid wall portions 29a, which form a boundary for a portion of the guide sections and extend beyond these sections, as shown in FIG. 1.

The lid slopes upwardly from the rib 25 and the guide section 27 around the periphery of the lid and then down again to define a groove 24 designed to receive a sealing gasket 26. The outer flange 31 or periphery of the lid flares outwardly and downwardly from the groove to enclose the base flange 18 when in closed position.

As shown in FIG. 2 the relatively large sealing gasket 26 has a generally vertical orientation with its base end 28 essentially potted or cast in place by the placement of liquid material of the same composition as the overall gasket itself so that the base end can be set within the liquid material wherein the gasket will be tightly held in place after the solidification of the liquid material. The groove 24 and gasket 26 may be further provided with a mating rib and groove to enhance the connection. The inner surface 32 of the vertical flexible portion 30 of the gasket is designed to mate with the outside surface 34 of the flange 18 on the base 14. The seal established between the lid and the base portion 14 results from the contact by the inside surface 32 of the gasket 26 and the outside surface 34 of the flange 18 on the base portion. It should be noted that as the lid 12 and the gasket 26 move closer to the flange 18 of the base, the vertically oriented, flexible end 30 of the gasket slides into further mating relationship with the angled flange 18. Consequently, the configuration of the angled flange 18 and the gasket 26 provides a good airtight seal which starts when the seal engages the flange 18, but improves as the lid is fully sealed. The combination of the distance between the gasket 26 and the top edge 16 of the base 14 in conjunction with the curved shape of the flange 18 and the flexible vertical end 30 of the gasket 26 provides a fairly wide tolerance range for the lid to fit onto the base and promotes the proper centering of the lid over the base as the seal is created between the gasket and the flange 18.

As shown in FIG. 1 and FIG. 4, located within the sidewall of the base 14 are recesses 36 which receive fuse members 38 at opposite longitudinal ends of the container. Each fuse member 38 fits within a recess 36 and extends above the top edge 16 of the base into a slot 29 in the lid between the guide sections 27 to contact a retaining nipple 40 located on the bottom surface 42 of the lid 12. The fuses 38 are of sufficient length so that when resting in the recesses 36 and contacting the centering nipple 40 on the lid, a space exists between the bottom tip 44 of the gasket 26 and the outside surface 34 of the depending flange 18 on the base 14. This space allows access of a sterilizing environment into the container when it is placed for instance within an autoclave. The fuses 38 each have a pair of notches 46 and 47 on opposite sides of their tubular shape. The fuses 38 are preferably made of material which when subjected to the temperatures above 275° F. for a predetermined period will lose its rigidity in holding the lid open and become more pliable, causing flexure adjacent the notches 46 and 47 to cause the collapse of the fuses and, as shown in FIG. 5, permitting the lid to sealingly engage with the base.

As shown in FIG. 2, located adjacent each of the lateral edges of the container is a biasing member 48 connected to the lid at one end 50 and connected to the base at the other end 52. The member 48 is preferably made of some type of plastic or silicone rubber material and produces a biasing of the lid toward the base. Consequently, the members 48 insure positive placement of the lid on the base as the fuses 38 weaken and collapse under the sterilizing environment of high temperature. Various biasing arrangements could be used connected between the lid and the base. In the present disclosure, the end 50 of the member 48 is enlarged to hold the member in a hole in the lid while the other end has a retaining rod 52 which snaps beneath a locking notch 56 on each end of the base in the depending flange 18.

Figure 3:
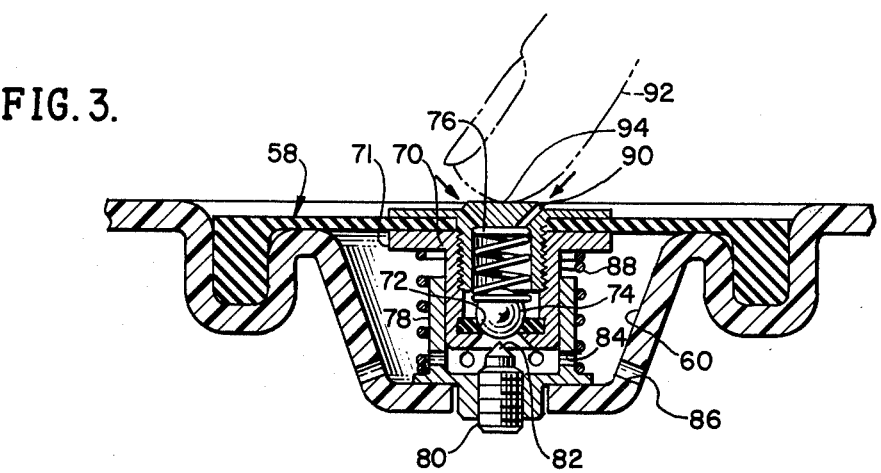
FIG. 3 is a sectional view taken along lines 3—3 in FIG. 2 illustrating the construction of the relief-release valve.

Located within the container lid 14 is a combination release and relief diaphragm valve 58 which is designed to provide relief if a vacuum formed in the container should become too great. This prevents any possible damage to the container itself. The valve also provides a release mechanism to enable a container under vacuum to be opened. As shown in FIGS. 2 and 3, the diaphragm valve 58 is a self-contained removable unit which fits within a circular recess 60 within the center of the lid. As shown in FIG. 3, the valve includes a diaphragm 64 having an enlarged periphery 66 which snaps into an annular groove 62 in the lid surrounding the central recess 60. The valve has a socket shaped main valve body 70 with a valve seat 72 on its lower end defining a valve orifice. The valve seat includes a washer of suitable material on which rests a ball valve member 74 biased downwardly against the seat 72 by a spring 76. The spring 76 and ball member 44 are held in position by a valve cap 71 which extends through the diaphragm 64 and threads into the upper end of the main valve body 70. The cap body 70 and the cap 71 mating flanges compress against the diaphragm so that the valve body and cap move with the diaphragm.

Located at the bottom of the recess 60 is a valve body guide 78 which guides movement of the valve body 70. Threaded into the guide 78 central bottom area is an adjustable plunger 80 having a contact point 82 designed to displace the ball valve 74, when the valve body 70 is depressed. A spring 88 surrounding the guide 78 and extending between the flange on the valve body 70 and a flange on the guide 78 urges the valve body 70 in its upward position and the guide 78 against the bottom of the recess 60. The area in the central recess 60 beneath the diaphragm 64 is in communication with the interior of the container by the loose fit between the guide 78 and recess 60 and the hole 61 in the lid recess wall and between the guide and the plunger 80. In addition, vent holes 84 in the guide 78 and the holes 86 in the lid insure proper communication.

Turning to the operation of the diaphragm valve 58, if a vacuum within the container becomes sufficiently great, the downward force on the diaphragm will overcome the bias of the plunger spring 88 so that the valve body 70 will move downward with respect to FIG. 3, causing the plunger point 82 to unseat the ball valve 74 from the seat 72. This allows the entrance of atmosphere through valve ports 90 in the valve cap 71 until the vacuum is reduced sufficiently to allow the plunger spring to again raise the valve body 70 so that the spring 76 can seat the ball valve. When the individual using the container decides to remove the sterilized instruments or other contents from the container, he depresses the valve cap 71 with his finger 92 sufficiently to cause the plunger point 82 to again unseat the ball valve 74 to allow air to enter through the valve ports 90 and into the container. The lid which previously was held tightly in place by the vacuum, can then be easily removed.

It should be noted that positioning the diaphragm valve 58 within the lid recess 60 provides a smooth flat, upper lid surface 22 which permits the stacking of several sealed containers. Furthermore, located on the bottom 96 of the base 14 are stacking legs 98 designed to fit within the top recess 100 of the lid 12 as shown in FIG. 4.

When the lid is in sealing engagement with the base 14 as shown in FIG. 2 it is envisioned that a heat shrunk plastic band will extend around the sealed container to provide additional means for maintaining the container closed as well as covering the diaphragm valve 58 to help prevent any inadvertent release of the vacuum within the container prior to the desired time of use of the articles contained therein. The band is approximately one inch wide and the material is the type which is flexible but will shrink and become more rigid when exposed to high temperatures and then cooled.

Consider now the overall operation and use of the container. Although the container is useful in various sterilizing environments, it is primarily intended for use in an autoclave which has a series of vacuum cycles and a heating cycle. When the container is in the open position as shown in FIG. 1, the instruments or articles to be sterilized are placed within the chamber 20 of the base 14, and the lid 12, with the respective fuses 38 at each of its longitudinal ends attached over the centering nipples 40, is lowered over the top edge 16 of the base portion 14 until the fuses 38 rest within the recesses 36. The guide sections 27 extend into the base a small amount, as shown in FIG. 4, to insure proper positioning of the lid. The retaining rods 52 of the biasing members 48 are positioned within the locking notches 56 on the downward flange 18 of the base 14. This causes a biasing force of the lid toward the base 14.

A band 102 of heat shrinkable material is placed around the container and aligned over the diaphragm valve 58. The container 10 is then placed within an autoclave or some other type of sterilizing unit where a penetrating sterilizing environment is introduced through the space between the gasket and the downward depending flange 18 of the base into the chamber 20 of the container to sterilize the instruments or articles therein. After a predetermined period of time of being exposed to extremely high temperatures in the range above 270° F. the ambiently rigid fuses 38 become much more pliable and will weaken under the change of the physical characteristic as well as the biasing force through the biasing member 48 to collapse at the notches 46 as shown in FIG. 5. Consequently, the lid will close onto the base 14 guided by the guides 27. The vertical flexible portion 30 of the gasket 26 will mate with the outside surface 34 of the flange 18 to produce a pneumatic seal between the lid and the base. It should be noted that the length of time to expose the sterilizing environment to the instruments within the container can be varied by changing the diameter and wall thickness of the fuses 38. Preferably, the fuses will collapse to allow the lid to close near the end of the last vacuum cycle in the autoclave while sterilizing temperature is still high. As the pressure surrounding the container rises, the lower pressure or vacuum in the container will further draw the lid closed until its rib 25 seats on the inside of the base upper edge 16, as seen in FIG. 2. The rib thus supports the side of the base. Cooling of the container also adds to the vacuum created within it. The overall design of the container lid and the base enhances the strength of the container to withstand any forces exerted by a vacuum. However, as a safety factor the diaphragm valve 58 in FIGS. 2 and 3 will reduce the vacuum if it becomes too great.

Heating of the band 102 and then later cooling it will cause the band to shrink around the container to provide additional security that the lid will remain closed. When the band shrinks, it also becomes somewhat rigid; and since it extends over the valve 58, it makes it difficult to operate the valve without removing the band. Since the valve is recessed in the lid, the band itself does not depress the valve cap 71. The material and characteristics of the band are well known and thus are not described in detail herein.

The sealed container can be placed in storage in stacked relationship with other containers for an indefinite period of time until the sterilized instruments or articles therein are needed for use. When the articles are needed, the container band 102 is cut, exposing the diaphragm valve 58. The valve when depressed by the individual will relieve the vacuum in the container and allow for the easy removal of the lid 12 when the retaining rods 52 of the members 48 are released from the base 14.

Although a variety of materials may be used for the container components, preferably a clear, rigid plastic that can handle the temperatures, such as, the container itself is made of polysulfone while the fuses are preferably made of polycarbonate. The gasket is preferably made of a silicone rubber which can handle temperatures up to 400° F. The members 48 are preferably made of a resilient silicone rubber. Instead of the separate members 48 it would be possible to just have a single member extend over the top or bottom of the lid and be connected just to the flange on opposite sides of the container. The materials used in the container are preferably all rust resistant and noncorrosive because of the steam autoclave environment.

What is claimed is:

1. A container adapted to be placed within an autoclave or other sterilizing environment and heated to sterilizing temperatures comprising a base and a lid defining a closed chamber, with said base and lid having mating peripheral portions, a plurality of posts extending between the lid and the base supporting the lid slightly spaced from the base so as to permit the flow of steam into the container, means on said base and said lid for receiving the ends of said posts in proper orientation extending between the base and the lid, said receiving means being within the interior of the containers but adjacent to said peripheral portions, and biasing means urging the lid into closed position against said posts, said posts positioning said lid directly above and aligned with the base and said posts being collapsible when subjected to sterilizing temperatures for a predetermined time so that the lid guided by said peripheral portions can be moved by said biasing means to the closed position on said base.

2. The container of claim 1 wherein said post is formed of a material which will begin to soften at sterilizing temperatures and including notch means formed in said post reducing the post cross-section in that area so the post will collapse first in the area of said notch means.

3. The container of claim 1 wherein said support means are arranged to space the entire lid slightly from the base, there being no other support for said lid.

4. The container of claim 1 wherein said mating peripheral portions include a downwardly and outwardly sloping flange formed on one of said lid and said base, and including a flexible gasket positioned between said flange and the other of said base and lid to provide a seal between the base and the lid, said gasket including a flexible free end which engages said flange in a manner such that the area of the gasket engaging said flange increases as the lid is drawn more tightly onto said base and such that fluid flow into the container is prevented.

5. The container of claim 1 including valve means formed in the lid for providing pressure release for said container, said valve means being automatically operable to limit the vacuum to be placed on the container and manually operable to equalize pressure between interior and exterior of the container.

6. The container of claim 1 wherein said predetermined time is at a point which will result in a vacuum in said container after the container has cooled to ambient temperature.

7. The apparatus of claim 1 including a band of heat shrinkable material wrapped around said container which loosely encircles the container before the container is subjected to said heat and which shrinks to tightly encircle said container after the container is heated and then cooled.

8. The combination comprising:
a container base and lid, defining a chamber, said lid having an outwardly facing recess formed therein and an opening in the wall of the recess so the chamber is open to said recess;
a flexible diaghragm extending across said recess so that one side of the diaphragm is exposed to pressure within the chamber and the other side is exposed to pressure outside the chamber;
a valve body attached to said diaphragm and having a valve seat defining an opening into said recess;
a valve member captured within said valve body urged into closing engagement with said valve seat;
means for biasing said diaphragm away from said recess;
a guide member surrounding said valve body and urged away from said valve body and towards said recess wall by said biasing means; and
unseating means mounted on said guide member and extending toward the opening in said valve seat for unseating said valve member when said diaphragm is moved into said recess toward said chamber either in response to an increase in exterior pressure relative to interior pressure, as sensed by said diaphragm, or in response to manually depressing said valve body.

9. A container adapted to be placed within an autoclave or other sterilizing environment and heated to sterilizing temperatures comprising a base and a lid defining a chamber, said base and lid having mating peripheral portions including a downwardly and outwardly sloping flange on one of said lid and base, and a gasket having one end tightly engaging the other of said lid and base and having a free, somewhat flat, flexible end extending toward the exterior of the container with one side of said free end exposed to the gaseous pressure on the interior of the container and engaging said flange to provide a seal between the base and the lid to prevent flow into the container, the flexibility of said free end and the slope of said flange permitting considerable closing movement of said lid onto said base after a seal is initially formed so that when the external pressure is increased relative to the internal pressure, the lid is moved further onto the base, increasing the sealing area and pressure between said gasket and flange, the other side of said free flexible end of said gasket being exposed to pressure on the exterior of the container so that a relative increase in pressure on the exterior of the gasket will further urge the gasket flexible end against said flange independently of any lid closing movement, said gasket and said mating peripheral portions being formed to guide said lid into proper closing position on the base, and temperature responsive means on said container for maintaining said container in unsealed condition until the container is subjected to sterilizing temperatures for a predetermined time.

10. A container adapted to be placed within sterilizing environment for holding items to be sterilized and stored, said container comprising a base and a lid defining a chamber, said base and lid having mating peripheral portions including a downwardly and outwardly sloping flange formed on one of said lid and base, and a gasket having one end tightly engaging the other of said lid and base and having a somewhat flat, free, flexible end extending toward the exterior of the container with one side of said free end being exposed to the container interior pressure and engaging said flange to provide a seal between the base and the lid to prevent flow into the container, the flexibility of said free end and the slope of said flange permitting considerable closing movement of said lid onto said base after a seal is initially formed so that when the pressure on the container exterior is increased relative to the internal pressure, the lid is moved further onto the base increasing the sealing area and pressure between said gasket and flange, the other side of said free flexible end of said gasket being exposed to pressure on the exterior of the container so that a relative increase in pressure on the exterior of the gasket will further urge the gasket flexible end against said flange independently of any lid closing movement, said gasket and said mating peripheral portions being formed to guide said lid into proper closing position on the base.

11. The container of claim 10 including means on said container for maintaining said container in unsealed condition until the container is subjected to said sterilizing environment for a predetermined time.

12. The container of claim 11 wherein said means for maintaining the container in unsealed condition is responsive to said environment to permit said container to seal.

13. A container adapted to be placed within a sterilizing environment comprising:
   a base and a lid defining a closed chamber with said lid and base having mating peripheral portions including a downwardly and outwardly sloping flange formed on one of said lid and said base;
   a flexible gasket positioned between said flange and the other of said lid and base, said gasket including a flexible free end wich engages said flange to prevent fluid flow past the gasket free end into the container; and
   means extending between said base and lid supporting the lid slightly spaced from said base to permit the flow of sterilizing environment into the container past said gasket free flexible end, said supporting means being responsive to said environment after a period of time to permit said lid to close as guided by said gasket and said peripheral portions to a position wherein one side of said gasket free end is exposed to the container interior and engages said flange to prevent flow past the gasket into the container, said gasket free end engaging said flange in a manner such that the area of the gasket engaging said flange increases as the lid is drawn more tightly into said base, the other side of said free end being exposed to pressure on the exterior of the container so that an increase in exterior pressure will further urge the flexible end of the gasket against said flange.

* * * * *